(12) United States Patent
Pujos et al.

(10) Patent No.: US 8,460,649 B2
(45) Date of Patent: Jun. 11, 2013

(54) *SACCHAROMYCES CEREVISIAE* STRAINS WITH PHYTOSANITARY CAPABILITIES

(75) Inventors: Philippe Pujos, Lille (FR); Didier Colavizza, Roubaix (FR); Pascal Vandekerckove, Villeneuve d'Ascq (FR)

(73) Assignee: Lesaffre et Compagnie, Paris (FR)

( * ) Notice: Subject to any disclaimer, the term of this patent is extended or adjusted under 35 U.S.C. 154(b) by 0 days.

(21) Appl. No.: 13/146,379

(22) PCT Filed: Jan. 26, 2010

(86) PCT No.: PCT/IB2010/050336
§ 371 (c)(1),
(2), (4) Date: Jul. 26, 2011

(87) PCT Pub. No.: WO2010/086790
PCT Pub. Date: Aug. 5, 2010

(65) Prior Publication Data
US 2011/0301030 A1    Dec. 8, 2011

(30) Foreign Application Priority Data
Jan. 27, 2009   (FR) ..................... 09 00339

(51) Int. Cl.
*A01N 63/04*    (2006.01)

(52) U.S. Cl.
USPC ....................................... 424/93.51

(58) Field of Classification Search
None
See application file for complete search history.

(56) References Cited

FOREIGN PATENT DOCUMENTS
FR    2 894 771 A1    6/2007
WO    2006/032530 A1    3/2006

OTHER PUBLICATIONS

International Search Report for App. No. PCT/IB2010/050336 dated May 6, 2010.

*Primary Examiner* — Suzanne M Noakes
(74) *Attorney, Agent, or Firm* — Sughrue Mion, PLLC

(57) ABSTRACT

The invention relates to a strain of *Saccharomyces cerivisiae* characterized in that it is selected from strain No. I-3936 deposited on Mar. 4, 2008 at the CNCM, strains No. I-3937 deposited on Mar. 4, 2008 at the CNCM, strain No. I-3938 deposited on Mar. 4, 2008 at the CNCM, and strain No. I-3939 deposited on Mar. 4, 2008 at the CNCM. The invention also relates to a phytosanitary composition and to a method for treating or protecting plants against diseases caused by pathogens, using said strain.

19 Claims, No Drawings

SACCHAROMYCES CEREVISIAE STRAINS WITH PHYTOSANITARY CAPABILITIES

CROSS REFERENCE TO RELATED APPLICATIONS

This application is a National Stage of International Application No. PCT/IB2010/050336 filed Jan. 26, 2010, claiming priority based on French patent application Ser. No. 09/00339 filed Jan. 27, 2009, the contents of all of which are incorporated herein by reference in their entirety.

FIELD OF THE INVENTION

The present invention relates to *Saccharomyces cerevisiae* yeasts useful as antagonistic microorganisms for protecting plants against various pathogens, notably fungi. The invention is adapted to the treatment of multiple plant varieties.

TECHNICAL BACKGROUND

Among pathogens of plants, fungi, responsible for fungal or cryptogamic diseases, are those which have the greatest economical impact. Each plant species is sensitive to one or several main diseases, which may strongly reduce its robustness, its growth and finally, the amounts or/and the quality of the harvest.

Various parameters influence the development of diseases such as the soil conditions and fertilization, the varietal sensitivity, the cultivation method (rotation, tillage, number of plants or seedlings per hectare, pruning system . . . ), or especially climate conditions. But acting on some of these parameters is not generally sufficient for sufficiently limiting the damages caused by the diseases. Also, as a guard against this, the practitioner who wishes to optimize and secure his/her yield, will treat his/her culture at the right time with a phytosanitary, often preventive, product. Most often, the products used are chemical products, most of which are highly efficient, but may represent health risks for personnel who handle them, and generate residues on treated productions, in the soils and waters. Further, repeated use of certain fungicidal active materials acting on the same metabolic site selects strains which are resistant to these fungicides.

In order to attempt to find a remedy to this, it is necessary to limit the number of yearly uses of chemicals of the same family, to alternate chemical families with different modes of action, and to use all other means unfavorable to the pathogen. In this context, there therefore exists a real and significant need for alternative solutions against plant diseases.

Ideally, these solutions should act in a way different from that of existing chemical fungicides, should not generate any chemical residues in the harvests and in the environment, and be safer and healthier for the operators. Such treatments should be used, either alone or alternately and/or in combination with present chemical treatments or any other treatment for preventing the occurrence or limiting the development of these pathogens and of their resistant strains, on the plants, and limit the risks for humans and the environment.

In this context, it is known how to administer antagonistic microorganisms toward pathogens to plants. For example, the microorganisms proposed hitherto as antagonistic microorganisms comprise the bacterium: *Bacillus subtilis*, the fungi: *Trichoderma harzanium, Trichoderma viride, Coniothyrium minitans, Streptomyces griseoviridis*, the yeasts: *Aureobasidium pullulans, Metschnikowia fructicola, Candida oleophila* . . . . The article "Biological control of post harvest diseases of fruits and vegetable" by El Ghaouth et al. (Applied Mycology and Biotechnology, Vol. 2, Agriculture and food production, Elsevier Science B.V., p. 219-238) proposes a review of what is known as regards biological control of pathogens on fruit, and proposes several possible explanations for the mode of action of antagonistic microorganisms.

The use of *Saccharomyces cerevisiae* yeasts as antagonistic microorganisms has also been contemplated. However, generally, the efficiency of these yeasts has been estimated as being lower than that of other microorganisms, or even in certain case nil. As an example, reference may be made to the article "Role of competition for sugars in yeasts in the biocontrol if gray mold in apples", by A. B. Filonow (Biocontrol Science and Technology, 8:243-256, 1998), which teaches that *Saccharomyces cerevisiae* is inefficient for reducing infection of apples by grey mold, unlike *Cryptococcus laurentii* and *Sporobolomyces roseus*.

Now, antagonistic microorganisms usually considered as the most efficient ones, are often isolated from the natural environment, are not well known, and may consequently express undesirable characteristics during their development or during their use. One is then faced with industrialization difficulties, or even with drawbacks toward humans or the environment.

Therefore, there exists a need for developing novel strains of antagonistic microorganisms, more reliable from an industrial point of view, safer from a health and environmental point of view, and efficient in controlling diseases caused by pathogens in plants.

SUMMARY OF THE INVENTION

The invention firstly relates to a strain of *Saccharomyces cerevisiae*, characterized in that it is selected from strain No. I-3936 deposited on Mar. 4, 2008, at the CNCM ("Collection Nationale de Cultures de Microorganismes"', Institut Pasteur, 25 rue du Docteur Roux, 75724 Paris Cedex 15, France), strain No. I-3927 deposited on Mar. 4, 2008 at the CNCM, strain No. I-3938 deposited on Mar. 4, 2008 at the CNCM and strain No. I-3939 deposited on Mar. 4, 2008 at the CNCM.

The invention also relates to a phytosanitary composition, comprising *Saccharomyces cerevisiae* yeasts selected from strain No. I-3936 deposited on Mar. 4, 2008 at the CNCM, strain No. I-3937 deposited on Mar. 4, 2008 at the CNCM, strain No. I-3938 deposited on Mar. 4, 2008 at the CNCM, strain No. I-3939 deposited on Mar. 4, 2008 at the CNCM and mixtures thereof.

According to an embodiment, the phytosanitary composition also comprises one or more formulation agents and/or at least one additional active adjuvant.

According to an embodiment, the phytosanitary composition is a concentrated phytosanitary composition, with a solid or liquid dry formulation.

According to an embodiment, the phytosanitary composition is a phytosanitary ready-to-use composition with a dry or liquid, preferably liquid formulation.

According to an embodiment, the phytosanitary composition comprises an amount of *Saccharomyces cerevisiae* yeasts comprised between $10^4$ and $10^{11}$ cfu/mL, preferably between $10^5$ and $10^{10}$ cfu/mL, more preferably between $5 \times 10^5$ and $5 \times 10^9$ cfu/mL.

The invention also relates to a method for treating or protecting plants against diseases caused by pathogens, comprising putting the plant into contact with *Saccharomyces cerevisiae* yeasts selected from strain No. I-3936 deposited on Mar. 4, 2008 at the CNCM, strain No. I-3937 deposited on Mar. 4, 2008 at the CNCM, strain No. I-3938 deposited on Mar. 4, 2008 at the CNCM and strain No. I-3939 deposited on Mar. 4, 2008 at the CNCM and mixtures thereof.

According to an embodiment, the pathogens are selected from fungi, viruses, bacteria, mycoplasms, spiroplasms, viroids and combinations thereof, preferably from fungi.

According to an embodiment, the pathogens are selected from microorganisms of the genera *Alternaria* spp., notably *Alternaria solani* and *Alternaria alternata*, *Ascochyta* spp., notably *Ascochyta fabae* or *Ascochyta pinodella*, *Aspergillus* spp., notably *Aspergillus niger* and *Aspergillus fumigatus*, *Botrytis* spp., notably *Botrytis cinerea*, *Bremia* spp., notably *Bremia lactucae*, *Cercospora* spp., notably *Cercospora beticola*, *Cladosporium* spp., notably *Cladosporium allii-cepae*, *Colletotrichum* spp., notably *Colletotrichum graminicola*, *Cryptosporiopsis* spp. notably *Cryptosporiopsis malicorticis*, *Erysiphe* spp., notably *Erysiphe graminis* or *necator*, *Fusarium* spp., notably *Fusarium oxysporum* and *Fusarium roseum*, *Gloeosporium* spp., notably *Gloeosporium fructigenum*, *Guignardia* spp., notably *Guignardia bidwellii*, *Helminthosporium* spp., notably *Helminthosporium tritici-repentis*, *Marssonina* spp., notably *Marssonina rosae*, *Monilia* spp., notably *Monilia fructigena*, *Mycosphaerella* spp., notably *Mycosphaerella brassicicola*, *Penicillium* spp., notably *Penicillium expansum* ou *Penicillium digitatum*, *Peronospora* spp., notably *Peronospora parasitica*, *Pezicula* spp. notably *Pezicula malicorticis*, *Phragmidium* spp., notably *Phragmidium rubi-idaei*, *Phytophtora* spp., notably *Phytophtora infestans*, *Plasmopara* spp., notably *Plasmopara viticola*, *Podosphaera* spp., notably *Podosphaera leucotricha*, *Pseudocercosporella* spp., including *Pseudocercosporella brassicae*, *Pseudoperonospora* spp., notably *Pseudoperonospora cubensis*, *Pseudopeziza* spp., notably *Pseudopeziza medicaginis*, *Puccinia* spp., notably *Puccinia graminis*, *Pythium* spp., *Ramularia* spp., notably *Ramularia betae*, *Rhizoctonia* spp., notably *Rhizoctonia solani*, *Rhizopus* spp., notably *Rhizopus nigricans* and *Rhizopus stolonifer*, *Rynchosporium* spp., notably *Rynchosporium secalis*, *Sclerotinia* spp., notably *Sclerotinia sclerotiorum*, *Septoria* spp., notably *Septoria nodorum* or *Septoria tritici*, *Sphaerotheca* spp., notably *Sphaerotheca macularis*, *Spilocaea* spp notably *Spilocaea pomi*, *Taphrina* spp., notably *Taphrina pruni*, *Trichothecium* spp. notably *roseum*, *Uncinula* spp., notably *Uncinula necator*, *Ustilago* spp., notably *Ustilago tritici*, *Venturia* spp., notably *Venturia inaequalis*, and combinations thereof, said pathogens being preferably selected from *Penicillium digitatum*, *Penicillium expansum*, *Botrytis cinerea* and combinations thereof.

According to an embodiment, the plants are selected from grasses, dicotyledonous plants, annual, biannual and perennial plants, seedlings of vegetables or harvested vegetables, plants or trees with fruit or the harvested fruit, plants or trees with flowers or the harvested flowers, cereals, oleaginous plants, proteaginous plants, ligneous plants, ornamental plants, and are notably selected from young plants or products stemming from potatoes, beetroot, sugar cane, tobacco, vines, wheat, rapeseed, barley, rice, maize, sorghum, millet, soya bean, beans, tomatoes, cucumbers, lettuces, strawberry plants, apple trees, pear trees, citrus fruit, bananas, pineapples, peach trees, apricot trees, cherry trees, walnut trees and hazelnut trees.

According to an embodiment, the aforementioned method comprises:
  applying the ready-to-use phytosanitary composition described above on all or part of the plants; or
  mixing the concentrated phytosanitary composition described above with a formulation agent in order to form a final phytosanitary composition, followed by applying this final phytosanitary composition on all or part of the plants.

According to an embodiment, applying the phytosanitary composition on all or part of the plants consists in applying it on the leaves, stems, flowers, fruits, trunks and/or roots or on a part thereof, preferably by spraying, the application on the roots being preferably carried out by ground spraying, mechanical incorporation, in a mixture with fertilizers, enriching agents or as a pre-mix.

The present invention makes it possible to overcome the drawbacks of the state of the art. More particularly it provides novel strains of antagonistic microorganisms, more reliable from an industrial point of view, safer from a health and environmental point of view and efficient for controlling diseases caused by pathogens in plants.

The invention is based on the development by the inventors of novel strains of *Saccharomyces cerevisiae* having very good phytosanitary capabilities. As *Saccharomyces cerevisiae* is a known yeast species and has been exploited for centuries by humans for producing bread or alcohol, including on an industrial scale, its use as an antagonistic microorganism is particularly advantageous.

Thus, efficient control against pathogens of plants and against the diseases which they cause is made possible, and this is done using products which are not or not very harmful for humans and for the environment, and easy to produce on an industrial scale.

According to particular embodiments, the invention also has one, or preferably several of the following advantageous features:
  the invention affords a long duration of plant protection (for example of more than 1 week, 2 weeks or 1 month) and a polyvalent action towards a plurality of pathogens;
  the invention is particularly applicable in the field of biological agriculture;
  the invention makes it possible to increase the global efficiency of plant protection, by reducing the infection level and/or reducing inoculum remission;
  the invention makes it possible limit the amount of residues of agrochemical products in or on the consumable products, in the soils and waters during the treatment of cultures or of a plant.

DESCRIPTION OF EMBODIMENTS OF THE INVENTION

The invention is now described in more detail and in a non-limiting way in the description which follows.

Types of Treatment (Curative or Preventive)

As indicated earlier, the invention relates to methods and products for preventively or curatively controlling pathogens in plants.

The relevant plants may be any type of plants and notably grasses and dicotyledonous plants, annual, biannual and perennial plants, vegetables, cereals including wheat, barley and rice, maize, sorghum, millet, oleaginous plants, proteaginous plants, potatoes, beetroots, sugar cane, tobacco, ligneous plants, fruit trees or non-fruit trees, vines, ornamental plants . . . .

According to a particular embodiment, the plants are fruit trees, for example seed-type fruit trees in particular selected from apple trees, pear trees and citrus fruit trees.

According to another embodiment, the plants are selected from vines, cereals (notably wheat), rapeseed, beetroots, potatoes, beans, tomatoes, cucumbers, lettuces or strawberry plants.

The term of "plants" used within the scope of the present invention covers both plants as such (for example fruit trees . . . ) and isolated portions of these plants, for example harvested fruit or flowers, but also grains or seeds (plant propagation material).

According to a particular embodiment, the plants are fruit, for example apples or pears or citrus fruit.

In the following, when putting plants into contact with a composition is mentioned, it should be understood that this putting into contact may be carried out on the whole or only on the portion of the surface of the plants. For example, when the plants are complete plants, the putting into contact may be carried out on the totality of the plants or on only one or more portions of the latter, such as for example, the leaves, stems, flowers, fruit, trunks and/or the roots or on only a portion of the surface of these leaves, stems, flowers, fruit, trunks and/or roots.

The products of the invention make it possible to efficiently protect plants against pathogens during a significant period of time, which may exceed one month, or even several months on fruit kept under cold conditions. Of course, repeated application may be contemplated at intervals to be defined by the user.

The invention may be applied for controlling any type of pathogens and notably fungi, viruses, bacteria, mycoplasms, spiroplasms or viroids. Control of fungi is made particularly efficient by the present invention.

As particular examples of pathogens, mention may notably be made of fungi of the genera *Alternaria* spp., for example *Alternaria solani* and *Alternaria alternate*, *Ascochyta* spp., for example *Ascochyta fabae* or *Ascochyta pinodella*, *Aspergillus* spp., notably *Aspergillus niger* and *Aspergillus fumigatus*, *Botrytis* spp., for example *Botrytis cinerea*, *Bremia* spp., for example *Bremia lactucae*, *Cercospora* spp., for example *Cercospora beticola*, *Cladosporium* spp., for example *Cladosporium allii-cepae*, *Colletotrichum* spp., for example *Colletotrichum graminicola*, *Cryptosporiopsis* spp. notably *Cryptosporiopsis malicorticis*, *Erysiphe* spp., for example *Erysiphe graminis* or *Erysiphe necator*, *Fusarium* spp., for example *Fusarium oxysporum* and *Fusarium roseum*, *Gloeosporium* spp., for example *Gloeosporium fructigenum*, *Guignardia* spp., for example *Guignardia bidwellii*, *Helminthosporium* spp., for example *Helminthosporium tritici-repentis*, *Marssonina* spp., for example *Marssonina rosae*, *Monilia* spp., for example *Monilia fructigena*, *Mycosphaerella* spp., for example *Mycosphaerella brassicicola*, *Penicillium* spp., for example *Penicillium expansum* or *Penicillium digitatum*, *Peronospora* spp., for example *Peronospora parasitica*, *Pezicula* spp. notably *Pezicula malicorticis*, *Phragmidium* spp., for example *Phragmidium rubi-idaei*, *Phytophtora* spp., including *Phytophtora infestans*, *Plasmopara* spp., including *Plasmopara viticola*, *Podosphaera* spp., for example *Podosphaera leucotricha*, *Pseudocercosporella* spp., including *Pseudocercosporella brassicae*, *Pseudoperonospora* spp., for example *Pseudoperonospora cubensis*, *Pseudopeziza* spp., for example *Pseudopeziza medicaginis*, *Puccinia* spp., including *Puccinia graminis*, *Pythium* spp., *Ramularia* spp., including *Ramularia betae*, *Rhizoctonia* spp., for example *Rhizoctonia solani*, *Rhizopus* spp., for example *Rhizopus nigricans* and *Rhizopus stolonifer*, *Rynchosporium* spp., like *Rynchosporium secalis*, *Sclerotinia* spp., like *Sclerotinia sclerotiorum*, *Septoria* spp., for example *Septoria nodorum* or *Septoria tritici*, *Sphaerotheca* spp., like *Sphaerotheca macularis*, *Spilocaea* spp. notably *Spilocaea pomi*, *Taphrina* spp., for example *Taphrina pruni*, *Trichothecium* spp. notably *Trichothecium roseum*, *Uncinula* spp., for example *Uncinula necator*, *Ustilago* spp., for example *Ustilago tritici* et *Venturia* spp., for example *Venturia inaequalis*. Combinations of the above pathogens may also be controlled by means of the invention.

*Penicillium digitatum*, *Penicillium expansum*, *Botrytis cinerea* are species against which the invention is particularly effective.

Examples of bacteria which affect cultures notably include the genera *Corynebacterium*, *Clavibacter*, *Curtobacterium*, *Streptomyces*, *Pseudomonas*, *Xanthomonas*, *Erwinia* spp. and particularly *Erwinia amylovora*, *Erwinia carotovora*, *Erwinia chrysanthemi*.

Examples of viruses affecting cultures are for example tobacco mosaic viruses, or the potato virus Y.

The invention offers a method for treating and/or protecting plants against diseases caused by the above pathogens, for example grey mold. The latter covers any curative or preventative method aiming at delaying or preventing the occurrence of these diseases, at eradicating them or at limiting or reducing the scale, the extent or the effects of these diseases.

Saccharomyces cerevisiae Strains as Antagonistic Microorganisms

By <<antagonistic microorganisms>>, is meant within the scope of the present invention a microorganism which is the antagonist of a pathogen, in particular of a pathogen likely to cause diseases in plants (notably a pathogen from the list above).

The invention offers four strains of *Saccharomyces cerevisiae* yeasts which are useful as antagonistic microorganisms, i.e.:
  strain No. I-3936 deposited on Mar. 4, 2008 at the CNCM;
  strain No. I-3937 deposited on Mar. 4, 2008 at the CNCM;
  strain No. I-3938 deposited on Mar. 4, 2008 at the CNCM; and
  strain No. I-3939 deposited on Mar. 4, 2008 at the CNCM.

The Use of Saccharomyces cerevisiae Strains of the Invention

The invention offers the use of the aforementioned *Saccharomyces cerevisiae* strains for protecting or treating plants against diseases caused by pathogens.

In particular, to do this, the invention provides a phytosanitary composition comprising one of the aforementioned *Saccharomyces cerevisiae* strains (or a mixture of several of these strains).

By <<phytosanitary composition>>, is meant within the scope of the present invention a composition capable of protecting plants against one or several pathogens and/or of treating plants infected by one or more pathogens.

The phytosanitary composition according to the invention may be in concentrated form or in a ready-to-use form. Said phytosanitary composition may be in a dry form, for example as powder or granules, or in liquid form, in particular in an aqueous form, for example as a suspension, a dispersion, a gel, a cream, a paste or in solid form. In the case of the ready-to-use composition, the aqueous liquid form is preferred, since this form is adapted to spraying.

In the case of a dry form, the yeasts of the aforementioned strains are preferably in dehydrated, freeze-dried and/or encapsulated form.

In the ready-to-use phytosanitary composition, the active material (*Saccharomyces cerevisiae* yeasts of the aforementioned strains) is already formulated in a suitable way for use on plants. Thus, the active material is for example mixed with an acceptable carrier, such as for example a liquid for filling a sprayer of the spray type, a fertilizer, a culture substrate for greenhouses . . . . The ready-to-use composition may be in powder form, but the liquid form is preferred.

Unlike the ready-to-use phytosanitary composition which is intended to be applied as such on plants, the concentrated phytosanitary composition is intended to be mixed with a formulation agent (carrier) by the user in order to form a final ready-to-use composition. Preferably, this formulation agent is water or an aqueous solution. Thus, typically, the user dissolves granules (concentrated phytosanitary composition) in water or dilutes an aqueous suspension or dispersion (concentrated phytosanitary composition) in water, in order to obtain the final ready-to-use composition.

If the yeasts are in dehydrated form in the concentrated phytosanitary composition and if the final composition is in liquid form (typically an aqueous form), customary precautions for rehydrating the yeast should be observed; for example the temperature of the formulation agent adapted to the dissolution/rehydration (typically water or an aqueous solution) is advantageously comprised between 20 and 25° C.

Whether the phytosanitary composition is concentrated or ready to use, in any case it generally comprises one or several solid or liquid formulation agents.

The formulation agent(s) may consist of any compound or of any inert material making it possible to facilitate or optimize transport, storage, handling, application and/or persistence of the active material on plants or on portions thereof. Such agents are adapted to the sought goal: preservation of active substances, maintenance of active substances in suspension during storage or during use in the preparation of the treatment mixture, anti-foaming, anti-dust, adhesion to plants, penetration into tissues, and other purposes. This or these agents may be solid, liquid, alone or in combination.

The formulation agent(s) may notably be selected from surfactants, dispersants, preservatives, wetting agents, emulsifiers, adhesion agents, pH buffers, nutrients either alone or mixed.

The amount of *Saccharomyces cerevisiae* yeasts which is applied to plants is defined by one skilled in the art, notably depending on the pathogen or the plurality of pathogens to be treated, on the type of plant, on the strain and on the combinations of strains used . . . . The amount applied is preferably sufficient for protecting the plants against a pathogen, or for limiting or suppressing the development and the effects of the pathogen which is present. This amount may for example be determined by field trials (or, for example when the plants are fruits, by laboratory tests or by tests in a fruit packing station on the fruit itself).

A ready-to-use phytosanitary composition preferably contains an amount of yeasts of the aforementioned strains comprised between $10^4$ and $10^{11}$ cfu/mL, preferably between $10^5$ and $10^{10}$ cfu/mL, more preferably between $5 \times 10^5$ and $5 \times 10^9$ cfu/mL.

The phytosanitary composition described above, in its final (ready-to-use) form may be applied to plants in different ways and according to different procedures or programs of treatments. In a preferred embodiment, the composition is liquid and is applied by spraying, notably by spraying leaves or the ground. In a particular embodiment, the composition is liquid and is applied by spraying onto harvested flowers or fruit.

Alternatively, it is possible to apply the composition as a mixture to fertilizers, culture supports, to sprinkling water, or other products. The composition may thus be administered to the roots by ground spraying, mechanical incorporation, mixing with fertilizers, enriching agents, as a pre-mix, or other means.

Other Possible Active Adjuvants

Within the scope of a preventive or curative treatment of plants against diseases causes by pathogens, other active adjuvants may be used. By <<active adjuvant>>, is meant any compound (different from the *Saccharomyces cerevisiae* yeasts of the aforementioned strains) capable of contributing to preventing or treating diseases of plants caused by pathogens, or capable of potentializing the effect of the *Saccharomyces cerevisiae* yeasts of the aforementioned strains in preventing or treating diseases of plants caused by pathogens.

According to an embodiment, these other active adjuvants may be included in the phytosanitary composition according to the invention.

According to another embodiment, these other active adjuvants may be administered to plants separately, as an additional treatment (sequentially or alternately).

These other relevant active adjuvants notably comprise:

1) Any antagonistic microorganism different from the *Saccharomyces cerevisiae* yeast of the aforementioned strains. Any known microorganism may be used as such as an antagonist of one or more pathogens of plants.

Preferably, the antagonistic microorganisms are selected from bacteria, fungi and yeasts, preferably yeasts.

The antagonistic microorganisms may in particular be selected from the group consisting of *Agrobacterium* spp., *Ampelomyces* spp., *Aureobasidium* spp., *Bacillus* spp., *Bulleromyces* spp., *Candida* spp., *Chaetomium* spp., *Coniothyrium* spp., *Cryptococcus* spp., *Debaryomyces* spp., *Dekkera* spp., *Erwinia* spp., *Exophilia* spp., *Gliocladium* spp., *Hansenula* spp. *Issatchenkia* spp., *Kluyveromyces* spp., *Mariannaea* spp., *Metschnikovia* spp., *Microdochium* spp., *Paecilomyces* spp, *Penicillium* spp., *Phlebiopsis* spp.; *Pichia* spp., *Pseudomonas* spp., *Pseudozyma* spp., *Pythium* spp., *Rhodotorula* spp., *Saccharomyces* spp., *Saccharomycopsis* spp., *Sporobolomyces* spp., *Streptomyces* spp., *Talaromyces* spp., *Trichoderma* spp., *Ulocladium* spp., *Verticilium* spp., *Zygosaccharomyces* spp. and mixtures thereof, and more particularly *Agrobacterium radiobacter, Aureobasidium pullulans, Bacillus subtilis, Bacillus licheniformis, Bacillus pumilis, Candida oleophila, Candida saitoana, Candida sake, Candida tenius, Candida utilis, Candida pefficulosa, Coniothyrium minitans, Cryptococcus albidus, Cryptococcus laurentii, Cryptococcus flavescens, Erwinia carotovora, Gliocladium catenalatum, Gliocladium virens, Hanseniaspora uvarum, Kluyveromyces thermotolerance, Metschnikovia fructicola, Metschnikowia pulcherrima, Metschnikowia reukafii, Microdochium dimerum, Paecilomyces fumosoroseus, Penicillium oxalicum, Phlebiopsis gigantean, Pichia anomala, Pichia guilliermondii, Pseudomonas cepacia, Pseudomonas chlororaphis, Pseudomonas fluorescens, Pseudomonas syringae, Pseudozyma flocullosa, Rhodotorula glutinis, Pythium oligandrum, Rhodotorula mucilaginosa, Saccharomyces cerevisiae, Saccharomycopsis schoeni, Streptomyces griseoviridis, Talaromyces flavus, Trichoderma atroviride, Trichoderma harzianum, Trichoderma polysporum, Trichoderma viride, Trichoderma asperellum, Trichoderma gamsi, Ulocladium atrum, Verticilium alboatrum*, and mixtures thereof.

2) Calcium, potassium or sodium salts.

Salts which are particularly efficient as active adjuvants are described in detail in document WO 2006/032530, to which reference is made.

In particular chloride, propionate, sulfate, phosphate, carbonate, bicarbonate, acetate, ethanoate, glycerate, glutamate, erythronate, theonate, ribonate, arabinoate, xylonate, lyxonate, allonate, altronate, gluconate, mannoate, gulonate, idonate, galactonate, talonate, alloheptonate, altroheptonate, glucoheptonate, mannoheptonate, guloheptonate, idoheptonate, galactoheptonate, taloheptonate, tartronate, malate, tartrate, citrate, saccharate, mucate, lactate, lactogluconate, ascorbate, isocitrate and citramalate salts of sodium or calcium or potassium (preferably calcium) are preferred, whether they are in an anhydrous or hydrate form.

Calcium lactate is particularly preferred. Mixtures of the above salts are also possible.

3) A stimulating agent selected from the group consisting of uronic acids, mannans, beta-1,3-glucan, mixtures and derivatives (salts, hydrates . . . ).

Galacturonic acid and glucoronic acid are preferred among uronic acids.

4) A fungicidal anti-viral and/or antibacterial agrochemical substance.

The fungicidal substance may be for example selected from organic agrochemical fungicides or inorganic mineral fungicides based on sulfur and/or copper.

Examples of presently available organic agrochemical fungicides are notably chloronitriles including chlorothalonil, carbamates including dithiocarbamates such as mancozeb, phthalimides including captan, sulfamides, guanidines, quinones, quinolines, thiadiazines, anilides, hydroxyanilides, and phenylamides, imidazolinones, oxazolidinediones, strobilurines, cyanoimidazoles, fluazinam, dinocap, sithiofam, dicarboximides, fludioxonil, organophosphorous compounds, propamocarb HCl, diphenylamine, pyridylamines, inhibitors of the biosynthesis of sterols (IBS), including imidazoles, pyrimidines, hydroxypyrimidines, anilinopyrimidines, triazoles, spiroxamine, morpholines and piperidines, fenhexamid, hymexazol, zoxamide, diethofencarb, benzimidazoles, pencycuron, quinoxyfen, iprovalicarb, cymoxanil, dimethomorph, phosphonates, triazines . . . .

The invention may also be used in alternation, association or combination with one or more compounds eliciting defenses in plants, such as for example b-aminobutyric acid, 2,6-dichloroisonicotinic acid, acibenzolar-s-methyl or certain algae extracts. Examples of such compounds are notably laminarin and ulvans.

In this respect, the invention also offers a method for preventing or slowing down the development of strains of fungi which are resistant to a family of fungicides, characterized in that the plants are treated with *Saccharomyces cerevisiae* yeasts of the aforementioned strains, as described above, with a view to reducing the selection pressure of strains resistant to said family of fungicides, or in that the treatment(s) of the plants with a substance from said family of fungicides is (are) alternated or combined with treatment(s) of plants with *Saccharomyces cerevisiae* yeasts of the aforementioned strains, as described above.

The invention also offers a method for preventing or slowing down the development of strains of bacteria which are resistant to a family of antibacterial agents, characterized in that the plants are treated with *Saccharomyces cerevisiae* yeasts of the aforementioned strains, as described above, with a view to reducing the selection pressure of the strains resistant to said family of antibacterial agents, or in that the treatment(s) of the plants with said antibacterial agent is (are) alternated or combined with treatment(s) of plants with *Saccharomyces cerevisiae* yeasts of the aforementioned strains, as described above.

However, according to a particular embodiment, the phytosanitary composition according to the invention is free of any fungicidal, antiviral and/or antibacterial substance which is toxic for *Saccharomyces cerevisiae* yeasts. According to a particular embodiment, no treatment by means of any fungicidal, antiviral and/or antibacterial agrochemical substance at a dose which is toxic for *Saccharomyces cerevisiae* yeasts is applied before the treatment by *Saccharomyces cerevisiae* yeasts of the aforementioned strains, except by observing the adequate waiting time.

EXAMPLES

The following examples illustrate the invention without limiting it.

Example 1

The efficiency of the present invention is tested against post-harvest fungal diseases, in the following way.

On grapefruit, three injuries are made per fruit. A phytosanitary composition is applied on each injury, it is left to dry, and then a composition containing a pathogen is inoculated.

The pathogen used is *Penicillium digitatum* at a concentration of $5 \times 10^4$ spores per mL.

After 4 or 5 days of incubation at 20° C., the average diameter of the lesions is measured.

The 4 following types of phytosanitary composition were used, with various concentrations of microorganisms (obtained by serial dilutions in sterile distilled water from a culture of microorganisms):

A: a composition containing strain No. I-3936 deposited on Mar. 4, 2008 at the CNCM.

B: a composition containing strain No. I-3937 deposited on Mar. 4, 2008 at the CNCM.

C: a composition containing strain No. I-3938 deposited on Mar. 4, 2008 at the CNCM.

D: a composition containing strain No. I-3939 deposited on Mar. 4, 2008 at the CNCM.

The strains of yeasts come from Lesaffre International (France).

The pathogen is obtained by isolation from rotten grapefruit; storage on tilted gelose of dextrose-potato at 4° C.; culture in tilted gelose dishes of dextrose-potato at 25° C.; removal of the spores of the sporulating edges of a 2-3 week culture; suspension in sterile distilled water and adjustment of the spore concentration with a hemacytometer.

Each test is averaged over 10 fruits.

The efficiency of the different preventive treatments is measured with respect to the untreated control and the results are shown in Table 1 below. The diameter of the lesions is measured at 4 days, except for the results marked with an asterisk (*), which are obtained at 5 days.

TABLE 1 prevention of infection by *Penicillium digitatum* on grapefruit

| Type of treatment | Yeast concentration (in cfu/mL) | Lesion diameter (in mm) | Efficiency (%) |
|---|---|---|---|
| Control | — | 77.78* | — |
| A | $4.08 \times 10^7$ | 24.07* | 69.0 |
| A | $4.08 \times 10^8$ | 5.56* | 92.9 |
| A | $4.08 \times 10^9$ | 0.00* | 100.0 |
| Control | — | 79.63 | — |
| A | $1.10 \times 10^7$ | 24.07 | 69.8 |
| A | $1.10 \times 10^8$ | 18.52 | 76.7 |
| A | $1.10 \times 10^9$ | 5.56 | 93.0 |
| B | $1.10 \times 10^7$ | 20.37 | 74.4 |
| B | $1.10 \times 10^8$ | 25.93 | 67.4 |
| B | $1.10 \times 10^9$ | 12.96 | 83.7 |
| Control | — | 83.33 | — |
| C | $3.12 \times 10^8$ | 27.78 | 66.7 |
| C | $3.12 \times 10^9$ | 5.56 | 93.3 |
| C | $3.12 \times 10^{10}$ | 0.00 | 100.0 |
| Control | — | 84.44 | — |
| D | $1.10 \times 10^7$ | 1.85 | 97.8 |
| D | $1.10 \times 10^8$ | 1.85 | 97.8 |
| D | $1.10 \times 10^9$ | 0.00 | 100.0 |

TABLE 1-continued prevention of infection by Penicillium digitatum on grapefruit

| Type of treatment | Yeast concentration (in cfu/mL) | Lesion diameter (in mm) | Efficiency (%) |
|---|---|---|---|
| Control | — | 90.74 | — |
| D | $1.08 \times 10^5$ | 75.93 | 16.3 |
| D | $1.08 \times 10^6$ | 37.78 | 58.4 |
| D | $1.08 \times 10^7$ | 7.41 | 91.8 |

Example 2

The same type of experiment as in Example 1 is repeated, except that apples are used instead of grapefruit, and that *Botrytis cinerea* (suspension of spores at a concentration of $10^6$ spores/mL) and *Penicillium expansum* (suspension of spores at a concentration of $10^5$ spores/mL) are used as pathogens. The assessment of the lesions is carried out 6 days after inoculation, the results are averaged on 15 fruits each time.

The results obtained against *Botrytis cinerea* are shown in Tables 2a and 2b below, and the results against *Penicillium expansum* are shown in the Tables 3a and 3b below.

TABLE 2a prevention of infection by Botrytis cinerea on apples

| Type of treatment | Yeast concentration (in cfu/mL) | Lesion diameter (in mm) | Efficiency (%) |
|---|---|---|---|
| Control | — | 21.4 | — |
| A | $10^7$ | 2.3 | 89.18 |
| A | $10^6$ | 9.4 | 55.88 |
| A | $10^5$ | 9.0 | 57.96 |
| B | $10^7$ | 6.9 | 67.64 |
| B | $10^6$ | 13.2 | 38.09 |
| B | $10^5$ | 11.6 | 45.58 |
| C | $10^7$ | 8.4 | 60.87 |
| C | $10^6$ | 11.2 | 47.66 |
| C | $10^5$ | 10.9 | 48.80 |

TABLE 2b prevention of infection by Botrytis cinerea on apples

| Type of treatment | Yeast concentration (in cfu/mL) | Lesion diameter (in mm) | Efficiency (%) |
|---|---|---|---|
| Control | — | 14.1 | — |
| A | $10^7$ | 4.3 | 69.56 |
| A | $10^8$ | 0.0 | 100 |
| D | $10^5$ | 5.6 | 60.57 |
| D | $10^6$ | 3.4 | 76.18 |
| D | $10^7$ | 2.7 | 80.91 |
| D | $5 \times 10^7$ | 0.8 | 94.16 |
| D | $10^8$ | 0.0 | 100 |

TABLE 3a prevention of infection by Penicillium expansum on apples

| Type of treatment | Yeast concentration (in cfu/mL) | Lesion diameter (in mm) | Efficiency (%) |
|---|---|---|---|
| Control | — | 16.9 | — |
| A | $10^7$ | 7.5 | 55.51 |
| A | $10^6$ | 7.3 | 56.69 |
| A | $10^5$ | 12.3 | 27.30 |
| B | $10^7$ | 12.2 | 28.08 |
| B | $10^6$ | 13.0 | 23.36 |
| B | $10^5$ | 14.0 | 17.19 |
| C | $10^7$ | 6.6 | 60.76 |
| C | $10^6$ | 9.4 | 44.62 |
| C | $10^5$ | 11.0 | 34.91 |

TABLE 3B prevention of infection by Penicillium expansum on apples

| Type of treatment | Yeast concentration (in cfu/mL) | Lesion diameter (in mm) | Efficiency (%) |
|---|---|---|---|
| Control | — | 24.0 | — |
| A | $10^7$ | 12.8 | 46.72 |
| A | $10^8$ | 3.8 | 84.0 |
| D | $10^5$ | 15.9 | 33.95 |
| D | $10^6$ | 15.2 | 36.73 |
| D | $10^7$ | 12.0 | 50.05 |
| D | $5 \cdot 10^7$ | 10.8 | 54.95 |
| D | $10^8$ | 7.2 | 70.12 |

Example 3

The same type of experiment as in Example 1 is repeated, except that eating grapes are used instead of grapefruit, and that *Botrytis cinerea* is used as a pathogen. Further, the efficiency of the protection by the yeasts is assessed by counting the number of infected grape berries per bunch, 7 days after inoculating the pathogen, so as to classify the bunches into 4 categories: (1) healthy bunch; (2) about 10% of the bunch is infected; (3) about 25% of the bunch is infected; (4) about 50% of the bunch is infected or more. The score of 0 is assigned to the category (1), 0.1 to category (2), 0.25 to category (3) and 0.6 to category (4), so as to calculate an average damage.

The results obtained on bunches of non-injured grapes are transferred into Table 4 below, and the results obtained on bunches of injured grapes are shown in Table 5 below.

TABLE 4 prevention of infection by Botrytis cinerea on non-injured eating grapes

| Treatment | Concentration (cfu/mL) | (1) | (2) | (3) | (4) | Average Damage | Efficiency (%) |
|---|---|---|---|---|---|---|---|
| Control | — | 0 | 0 | 2 | 3 | 0.46 | — |
| B | $10^7$ | 1 | 0 | 2 | 2 | 0.34 | 26.1 |
| C | $10^7$ | 0 | 3 | 2 | 0 | 0.16 | 65.2 |
| D | $10^7$ | 1 | 3 | 1 | 0 | 0.11 | 76.1 |
| B | $10^6$ | 0 | 1 | 4 | 0 | 0.22 | 52.2 |
| C | $10^6$ | 0 | 0 | 4 | 1 | 0.32 | 30.4 |
| D | $10^6$ | 0 | 1 | 2 | 2 | 0.36 | 21.7 |

TABLE 5 prevention of infection by *Botrytis cinerea* on injured eating grapes

| Treatment | Concentration (ufc/mL) | (1) | (2) | (3) | (4) | Average Damage | Efficiency (%) |
|---|---|---|---|---|---|---|---|
| Control | — | 0 | 0 | 4 | 1 | 0.32 | — |
| B | $10^7$ | 0 | 1 | 3 | 1 | 0.29 | 9.4 |
| C | $10^7$ | 0 | 2 | 3 | 0 | 0.19 | 40.6 |
| D | $10^7$ | 0 | 4 | 1 | 0 | 0.13 | 59.4 |
| B | $10^6$ | 0 | 1 | 3 | 1 | 0.29 | 9.4 |
| C | $10^6$ | 0 | 2 | 3 | 0 | 0.19 | 40.6 |
| D | $10^6$ | 0 | 4 | 1 | 0 | 0.13 | 59.4 |

Example 4

This experiment was conducted under real conditions, in the field and in the fruit packing station. In an orchard of nectarines, of the Fantasia variety, 10 trees were identified and numbered, including 5 which are not treated and 5 which are.

The treatment mixture (ready-to-use phytosanitary composition) was prepared by dispersion in water at 20° C. of dried yeast granules with instantaneous dispersion, at a concentration of 25 g/L. The strain used for producing these granules was strain A.

The fruits were treated on the tree, the day before harvesting, after having removed the rotten fruit. Upon harvesting, the trays were marked with the tree number and entered into a refrigerated cell.

The fruits were kept for one week under cold conditions (4° C.), and then kept at normal temperature (about 25° C.) for 3 days in order to promote development of diseases. The scorings were then carried out. When spots of *monilia fructigena* or *botrytis cinerea* were present, their number and their diameter in mm were recorded, for each of the observed fruit.

Finally, the number of healthy fruits, the number of spotted fruits, the percentage of healthy fruit and of spotted fruit, the average number of spots per fruit, the average diameter of the spots were calculated. The efficiency according to Abott was calculated on the percentages of spotted fruit, the average number of spots and the average diameter of the spots. The results are shown in Table 6 below.

TABLE 5 phytosanitary effect under harvesting conditions

| | Harvested fruit | Spotted fruit | Healthy fruit | Fungal spots | Spot diameter in mm |
|---|---|---|---|---|---|
| Non-treated | | | | | |
| Number of fruits | 267 | 202 | 65 | | |
| % | 100 | 75.7 | 24.3 | | |
| Total number | | | | 349 | |
| Number/spotted fruit | | | | 1.73 | |
| Sum of the diameters | | | | | 16309 |
| Average diameter | | | | | 46.7 |
| Treated | | | | | |
| Number | 235 | 114 | 121 | | |
| % | 100 | 48.5 | 51.5 | | |
| Total number | | | | 180 | |
| Number/spotted fruit | | | | 1.58 | |
| Sum of the diameters | | | | | 7779 |
| Average diameter | | | | | 43.2 |
| Efficiency (%) | | 35.9 | | 8.6 | 7.5 |

The invention claimed is:

1. A phytosanitary composition comprising a *Saccharomyces cerevisiae* yeast from at least one isolated *Saccharomyces cerevisiae* strain selected from strain No. I-3936 deposited on Mar. 4, 2008 at the CNCM, strain No. I-3937 deposited on Mar. 4, 2008 at the CNCM, and strain No. I-3938 deposited on Mar. 4, 2008 at the CNCM, and strain No. I-3939 deposited on Mar. 4, 2008 at the CNCM.

2. The phytosanitary composition according to claim 1, further comprising one or more formulation agents and/or at least one additional active adjuvant.

3. The phytosanitary composition according to claim 1, wherein said composition is concentrated and is dry, solid or liquid.

4. The phytosanitary composition according to claim 1, wherein said composition is a ready-to-use dry or liquid phytosanitary composition.

5. The phytosanitary composition according to claim 4, comprising an amount of said yeast comprised between $10^4$ and $10^{11}$ cfu/mL.

6. A method for treating or protecting plants against diseases caused by pathogens, comprising putting plants into contact with a *Saccharomyces cerevisiae* yeast selected from strain No. I-3936 deposited on Mar. 4, 2008 at the CNCM, strain No. I-3937 deposited on Mar. 4, 2008 at the CNCM, strain No. I-3938 deposited on Mar. 4, 2008 at the CNCM, and strain No. I-3939 deposited on Mar. 4, 2008 at the CNCM, and mixtures thereof, or into contact with a phytosanitary composition according to claim 1.

7. The method according to claim 6, wherein the pathogens are selected from fungi, viruses, bacteria, mycoplasms, spiroplasms, viroids and combinations thereof.

8. The method according to claim 6, wherein the pathogens are selected from microorganisms of the genera *Alternaria* spp., *Ascochyta* spp., *Aspergillus* spp., *Botrytis* spp., *Bremia* spp., *Cercospora* spp., *Cladosporium* spp., *Colletotrichum* spp., *Cryptosporiopsis* spp., *Erysiphe* spp., *Fusarium* spp., *Gloeosporium* spp., *Guignardia* spp., *Helminthosporium* spp., *Marssonina* spp., *Monilia* spp., *Mycosphaerella* spp., *Penicillium* spp., *Peronospora* spp., *Pezicula* spp., *Phragmidium* spp., *Phytophtora* spp., *Plasmopara* spp., *Podosphaera* spp., *Pseudocercosporella* spp., *Pseudoperonospora* spp., *Pseudopeziza* spp., *Puccinia* spp., *Pythium* spp., *Ramularia* spp., *Rhizoctonia* spp., *Rhizopus* spp., *Rynchosporium* spp., *Sclerotinia* spp., *Septoria* spp., *Sphaerotheca* spp., *Spilocaea* spp., *Taphrina* spp., *Trichothecium* spp., *Uncinula* spp., *Ustilago* spp., *Venturia* spp., and combinations thereof.

9. The method according to claim 6, wherein the plants are selected from grasses, dicotyledonous plants, annual plants, biannual plants, perennial plants, vegetal seedlings, harvested vegetables, fruit plants, fruit trees, harvested fruits, flower plants, flower trees, harvested flowers, cereals, oleaginous plants, proteaginous plants, ligneous plants, and ornamental plants.

10. The method according to claim 6, comprising:
applying the ready-to-use phytosanitary composition according to claim 4 or 5 on all or part of the plants; or
mixing the concentrated phytosanitary composition according to claim 3 with a formulation agent in order to form a phytosanitary composition, followed by applying this final phytosanitary composition one all or part of the plants.

11. The method according to claim 10, wherein the application of the phytosanitary composition on all or part of the plants consists of applying said composition on the leaves, stems, flowers, fruit, grain, seed, trunk and/or roots or on part thereof.

12. The phytosanitary composition according to claim 4, wherein said composition is a liquid formulation.

13. The phytosanitary composition according to claim 5, comprising an amount of said yeast comprised between $10^5$ and $10^{10}$ cfu/mL.

14. The phytosanitary composition according to claim 5, comprising an amount of said yeast comprised between $5\times10^5$ and $5\times10^9$ cfu/mL.

15. The phytosanitary composition according to claim 7, wherein the pathogen is selected from fungi.

16. The method according to claim 8, wherein the pathogens are selected from *Alternaria solani, Alternaria alternata, Ascochyta fabae, Ascochyta pinodella, Aspergillus niger, Aspergillus fumigatus, Botrytis cinerea, Bremia lactucae, Cercospora beticola, Cladosporium allii-cepae, Colletotrichum graminicola, Cryptosporiopsis malicorticis, Erysiphe graminis, necator, Fusarium oxysporum, Fusarium roseum, Gloeosporium fructigenum, Guignardia bidwellii, Helminthosporium tritici-repentis, Marssonina rosae, Monilia fructigena, Mycosphaerella brassicicola, Penicillium expansum, Penicillium digitatum, Peronospora parasitica, Pezicula malicorticis, Phragmidium rubi-idaei, Phytophtora infestans, Plasmopara viticola, Podosphaera leucotricha, Pseudocercosporella brassicae, Pseudoperonospora cubensis, Pseudopeziza medicaginis, Puccinia graminis, Ramularia betae, Rhizoctonia solani, Rhizopus nigricans, Rhizopus stolonifer, Rynchosporium secalis, Sclerotinia sclerotiorum, Septoria nodorum, Septoria tritici, Sphaerotheca macularis, Spilocaea pomi, Taphrina pruni, roseum, Uncinula necator, Ustilago tritici,* and *Venturia inaequalis*.

17. The method according to claim 16, wherein the pathogens are selected from *Penicillium digitatum, Penicillium expansum, Botrytis cinerea, Monilia fructigena* and combinations thereof.

18. The method according to claim 9, wherein the plants are selected from seedlings or products from potatoes, beetroots, sugar cane, tobacco, vine, wheat, rapeseed, barley, rice, maize, sorghum, millet soya bean, beans, tomatoes, cucumbers, lettuces, strawberry plants, apple trees, pear trees, citrus fruit, banana, pineapple, peach trees, apricot trees, cherry trees, walnut trees and hazelnut trees.

19. The method according to claim 11, wherein the application of the phytosanitary composition is carried out by ground spraying, mechanical incorporation, by mixing with fertilizers, enriching agents or as a premix.

* * * * *